United States Patent [19]
Lee et al.

[11] Patent Number: 5,445,964
[45] Date of Patent: Aug. 29, 1995

[54] DYNAMIC ENGINE OIL AND FUEL CONSUMPTION MEASUREMENTS USING TUNABLE DIODE LASER SPECTROSCOPY

[76] Inventors: Peter S. Lee, 1590 Martinique Dr., Troy, Mich. 48084; Joseph A. Vitale, Jr., 52500 Southdown, Shelby Township, Macomb County, Mich. 48316; Richard F. Majkowski, 155 N. Harbor Dr., Chicago, Ill. 60601

[21] Appl. No.: 241,421
[22] Filed: May 11, 1994
[51] Int. Cl.⁶ ............................................. G01N 21/61
[52] U.S. Cl. ..................................... 436/60; 436/101; 436/124; 436/143; 436/171; 250/343
[58] Field of Search ................. 436/56, 60, 101, 124, 436/171, 181, 143; 250/339.13, 340, 341, 343

[56] References Cited
U.S. PATENT DOCUMENTS

| | | | |
|---|---|---|---|
| 4,338,570 | 7/1982 | Kurnit | 330/4.6 |
| 4,439,860 | 3/1984 | Kurnit | 372/70 |
| 4,990,780 | 2/1991 | Lee et al. | 250/343 |
| 5,030,329 | 7/1991 | Haidle et al. | 204/9 |
| 5,173,749 | 12/1992 | Tell et al. | 356/437 |

Primary Examiner—Jeffrey R. Snay
Attorney, Agent, or Firm—George A. Grove

[57] ABSTRACT

A method is provided for precisely and concurrently measuring dynamic engine oil consumption and fuel consumption within an internal combustion engine on a real-time basis. Nonradioactive organo-bromine or chlorine compounds are added to the oil in small amounts in their natural isotopic abundance or enriched. Upon complete combustion, the bromine or chlorine is converted into hydrogen bromide (HBr) or hydrogen chloride (HCl), respectively. A tunable diode laser spectrometer is used to determine the trace amounts of the resultant HBr or HCl in the exhaust gases, which continuously flows through a sample cell by the use of a sample line that allows the unimpeded transport of samples, reduces the pressure of the exhaust gas and maintains it at a suitable level for analysis, and prevents the condensation of water vapor in the exhaust gas so as to prevent the dissolution of the tracer compounds in the water condensate.

12 Claims, 2 Drawing Sheets

DYNAMIC ENGINE OIL AND FUEL CONSUMPTION MEASUREMENTS USING TUNABLE DIODE LASER SPECTROSCOPY

This invention relates to a method for determining fuel and engine oil consumption in an internal combustion engine. More particularly, this invention relates to a method for determining such consumption which utilizes laser spectroscopy of nonradioactive tracer compounds.

BACKGROUND OF THE INVENTION

For evaluating the performance of an internal combustion engine and the corresponding engine design development, it is desirable to provide dynamic measurements of fuel and engine oil consumption during operation of the internal combustion engine. Currently, the available methods for determining oil consumption are primarily (1) the use of a dipstick, (2) drain-weigh techniques, (3) radiometric techniques and (4) sulfur methods. However, there are serious shortcomings particular to each of these methods. In addition, there are shortcomings common to all of these methods such as their failure to provide real-time analysis of oil consumption and their failure to provide information on related fuel consumption during the engine operation.

With regard to the traditional dipstick and drain-weigh techniques, many hours of engine operation are required before enough oil is consumed to obtain repeatable and predictable measurements using these rather imprecise methods. As an example, if it is assumed that an engine operating at 50 miles per hour will consume oil at the rate of approximately 5000 miles per quart, the oil consumption rate will be about 0.01 quart of oil per hour. Due to the excessive periods of operation required before measurements may be made using these techniques, information on the time resolution of engine operation is prohibited. In addition, these techniques are susceptible to a high degree of inaccuracy, since any losses due to oil seal leaks or retention of the oil on surfaces within the engine will lead to an overestimate of oil consumption, while an underestimate of oil consumption may occur due to fuel dissolution with the oil.

There are also methods for determining oil consumption which rely on the monitoring of sulfur dioxide ($SO_2$), either photometrically or coulometrically, generated from the sulfur in the engine oil during engine operation. This method requires sulfur-free isooctane fuel, which therefore undesirably limits the adaptability of this method. In addition, extensive equipment and manpower are required to maintain the test system. Lastly, this method is also subject to interferences from other major or minor exhaust gas components.

The radiometric method is also known and employed by the art and provides a very precise method for measuring oil consumption. This method involves adding the radioactive bromine tracer 1,2-dibromooctadecane to the oil. The resultant combustion product from the internal combustion engine is trapped within a sodium hydroxide solution and counted by scintillation counting. Though extremely accurate, this method is undesirable because of the significant radioactive health and safety considerations and regulatory requirements necessary for its use. In addition, another shortcoming of this method is that it is essentially a batch process which does not readily lend itself to individual measurements, and further requires the preparation of a fresh bromine tracer for each batch operation because of the short half life of the radioactive bromine tracer.

As a solution to the above, U.S. Pat. No. 4,990,780 to Lee et al., which is assigned to the assignee of this invention, provides a novel method for determining oil consumption which is relatively simple and precise, enables real-time measurements, and additionally provides concurrent dynamic fuel consumption data. Lee et al. utilize nonradioactive tracer compounds, such as bromine or chlorine in the form of organic bromo- or chloro-compounds, which are added to the engine oil in small amounts. Upon complete combustion, the bromine or chlorine is converted into hydrogen bromide (HBr) or hydrogen chloride (HCl), respectively. A sample of the exhaust gases generated by the internal combustion engine and comprising the hydrogen bromide or hydrogen chloride is then collected within a sample cell, where the gas sample is maintained at a pressure at which a distinction between an absorption line of the tracer specie and the absorption lines of a related isotopic species can be discerned. Monochromatic radiation is then transmitted through the gas sample at the frequency of an absorption line for the tracer specie. Tunable diode laser spectroscopy is preferably used to measure the amount of tracer isotope within the resultant HBr or HCl gases in the exhaust gases. Lee et al. teach that this same technique may also be used to determine the corresponding fuel consumption from the $CO_2$ in the exhaust gases.

In use, several shortcomings have generally been identified regarding the system taught by Lee et al. When using a bromine compound, for example, it was determined that a filter required to protect the sample cell from contaminants within the exhaust gas tended to block and retain the hydrogen bromide, thereby possibly preventing the detection of a signal for hydrogen bromide in the exhaust gas. A major problem identified was that the hydrogen bromide was being lost through dissolution in water that had condensed in the sample line upstream of the sample cell, resulting in a total loss of the tracer signal. Such a problem is exacerbated by the desire to minimize the amount of tracer element present in the oil and also the high amount of water vapor present in the exhaust gas of an internal combustion engine.

Therefore, it would be desirable if improvements in the teachings of Lee et al. could be achieved by which the sample cell could be protected from contaminants, and water condensation could be substantially eliminated upstream of the sample cell, so as to provide a method by which minute amounts of gaseous hydrogen bromide or hydrogen chloride would be present and detectable, even in the presence of a large amount of exhaust water vapor.

SUMMARY OF THE INVENTION

It is an object of the present invention to provide a method for concurrently measuring fuel and engine oil consumption in an internal combustion engine, whereby concurrent, real-time, simple and precise measurements of fuel and engine oil consumption can be made, all without undue health and safety concerns.

It is another object of this invention that such a method utilize a tunable diode laser spectrometer for analyzing nonradioactive tracer elements within an exhaust gas sample that has been passed through a sample cell.

It is yet another object of this invention that such a method protect the sample cell from contaminants within the exhaust gas without the use of filters which significantly block and retain the tracer element.

It is a further object of this invention that such a method substantially prevent the condensation of water upstream of the sample cell, so as to substantially prevent the dissolution of the tracer element in the water condensate.

In accordance with a preferred embodiment of this invention, these and other objects and advantages are accomplished as follows.

A method is provided for precisely and concurrently measuring dynamic engine oil consumption and fuel consumption within an internal combustion engine in an automotive environment on a real-time basis. As such, the method of this invention provides significant input to the testing of engine design parameters and engine performance under realistic operating conditions.

Generally, the method is an improvement over the teachings of U.S. Pat. No. 4,990,780 to Lee et al., and uses nonradioactive organic bromo- or chloro-compounds which are added to the engine oil in small amounts in order to serve as tracer compounds. Upon complete combustion, the bromine or chlorine is converted into hydrogen bromide (HBr) or hydrogen chloride (HCl), respectively. A sample of the exhaust gases generated by the internal combustion engine, and containing the hydrogen bromide or hydrogen chloride, continuously flows through a sample cell and is maintained at a pressure within the sample cell where distinction between an absorption line of the tracer specie and the absorption lines of a related isotopic species is discernible. Monochromatic radiation is then transmitted through the gaseous sample at the frequency of an absorption line for the tracer specie. Because of the high spectral power density and spectral resolution of the preferred tunable diode lasers, tunable diode laser spectroscopy is preferably used to measure the trace amount of the resultant HBr or HCl gases in the exhaust gases.

As an improvement to the teachings of Lee et al., the method of this invention further contemplates the use of a sample line which serves to protect the sample cell from exhaust gas contaminants, as well as prevent the condensation of water vapor in the exhaust gas, so as to prevent the dissolution of the tracer compounds in the water condensate. In particular, the sample line utilizes a small orifice by which the pressure of an exhaust gas sample is reduced, in conjunction with a heated section immediately downstream of the orifice which prevents water vapor in the rapidly expanded exhaust gas from condensing. As a result, proper flow through the sample cell and proper pressure within the sample cell can be achieved, such that the tracer compound and water vapor coexist in the sample gas during analysis. Furthermore, the sample line has been found to substantially eliminate particulate matter within the exhaust gas. As a result, contamination of the optical components of the sample cell can be substantially prevented without the use of filters upstream of the sample cell, which would otherwise significantly block and retain the tracer element.

Other objects and advantages of this invention will be better appreciated from a derailed description thereof which follows.

BRIEF DESCRIPTION OF THE DRAWINGS

Reference will be made to the accompanying drawings wherein.

DETAILED DESCRIPTION OF THE INVENTION

Figure 1:
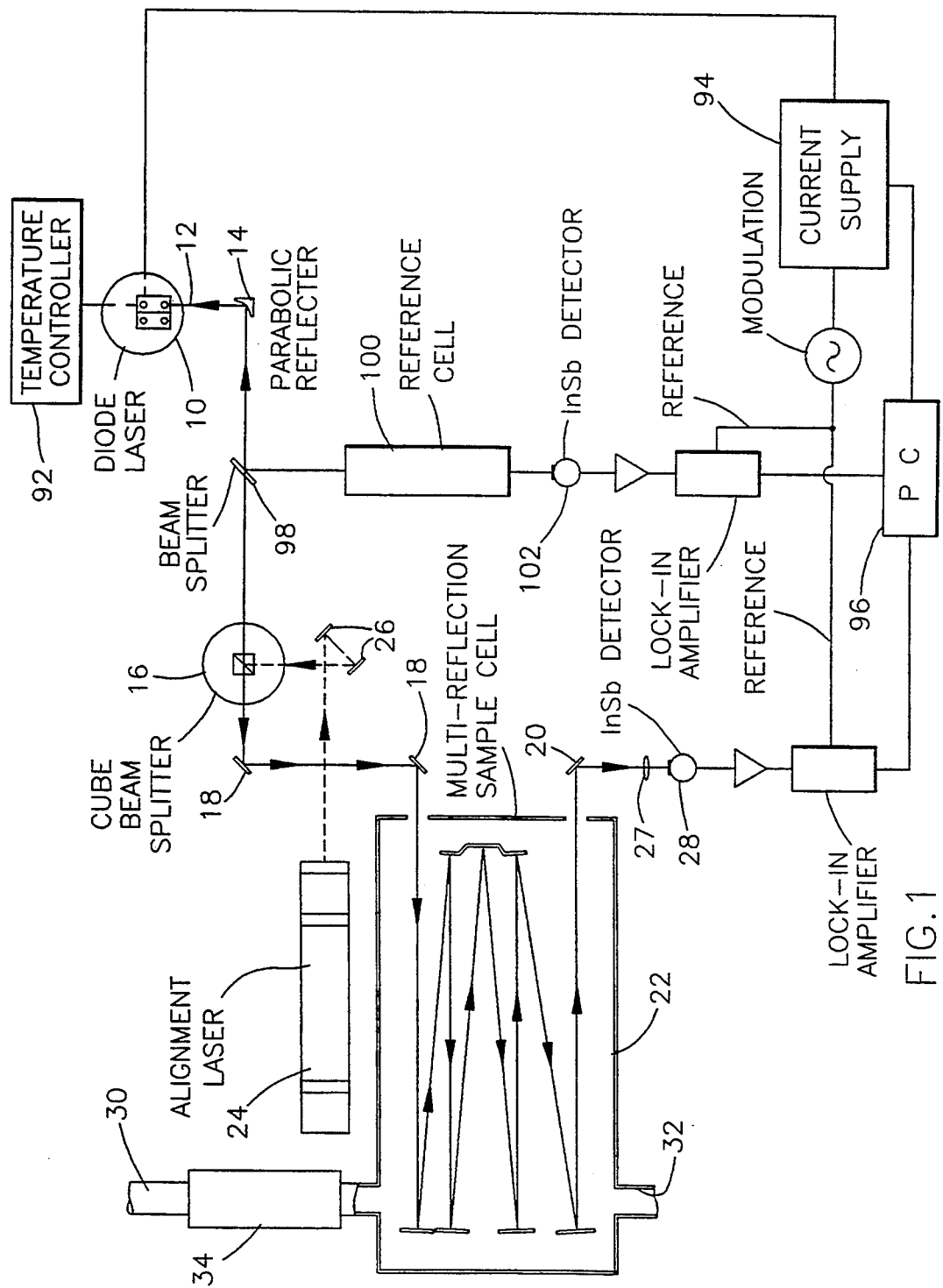
FIG. 1 is a schematic of a tunable diode laser spectrometer system in accordance with a first embodiment of this invention.

In accordance with this invention, as well as the teachings of U.S. Pat. No. 4,990,780 to Lee et al., nonradioactive stable organobromo or organochloro compounds are added to the oil of an internal combustion engine for the purpose of forming a tracer compound by which oil or gas consumption can be determined for the engine. The organobromo or organochloro compounds are matched to the volatility of the engine oil and are added to the oil in small amounts as in their natural isotopic abundance or as in an enriched state. Upon complete combustion, the bromine or chlorine is converted into hydrogen bromide (HBr) or hydrogen chloride (HCl), respectively. A tunable diode laser spectrometer is used to determine the trace amount of the resultant HBr or HCl of the exhaust gases. The tunable diode laser is characterized by a high spectral power density and spectral resolution better than approximately 0.0001 of a wave number. In addition, during operation of an automobile, the ratio of fuel-to-oil consumption is generally about 1000:1. Therefore, virtually all of the carbon dioxide found in the exhaust comes from the combustion of fuel. Simultaneous detection and measurement of exhaust carbon dioxide accordingly provides useful information on fuel consumption.

The expected concentration of HBr or HCl in the exhaust gas may be determined from the following assumptions. Assuming that the fuel economy of an automobile is approximately 20 miles per gallon at a speed of about 50 miles per hour, and further assuming that about 5000 miles per quart is the typical oil consumption, then the oil consumption rate for the automobile would be expected to be approximately 0.17 milliliters per minute. In addition, the air-to-fuel mass ratio during the operation of an automobile's internal combustion engine is typically about 14.5:1. The exhaust volume may be estimated by this intake air flow. Thus, for an automobile operating at a speed of approximately 50 miles per hour and consuming approximately 20 miles per gallon of fuel, the exhaust flow is estimated to be approximately 1542 liters per minute at standard temperature and pressure, assuming about 750 grams per liter is the density of fuel and about 1.293 grams per liter is the density of air at standard temperature and pressure.

In conventional radiometric methods which use a radioactive bromine compound for determining oil consumption, the total amount of bromine added to the fuel is typically about 0.05 weight percent. The bromine is usually provided in the form of a radioactive organobromine compound such as 1,2-dibromooctadecane.

Therefore, for the laser spectroscopy method of this invention, if the same amount of a nonradioactive bromine compound is added to the oil, the amount of hydrogen bromide in the exhaust gas would be expected to be approximately:

0.17 ml/min×0.84 gm/ml×0.05%×22.4 liter/mole÷80 gm/mole=2×10$^{-5}$ liters per minute at standard temperature and pressure, assuming the density of oil is about 0.84 grams per milliliter, the estimated oil consumption rate is about 0.17 milliliters per minute, and the atomic weight of bromine is about 80 grams per mole. From the above numbers, the concentration of exhaust hydrogen bromide can be estimated to be approximately:

2×10$^{-5}$ liter/min÷1542 liter/min≈13.0×10$^{-9}$

Therefore, the amount of HBr in the exhaust gases is approximately 13 parts per billion (volume).

For the same amount of chlorine, i.e., approximately 0.05 weight percent in the oil, in the form of an organochlorine compound such as 1,2 dichlorooctadecane or an organochlorine compound with a carbon number in the range of 18 to 35, the expected concentration of hydrogen chloride in the exhaust is estimated to be approximately 29 parts per billion, using the analogous calculations and assumptions used above for the bromine compound. These minute levels are detectable and measurable using the laser spectrometer system of this invention due to the high spectral power density and spectral resolution of the laser spectrometer. The measurements may be made even simpler if the amount of organobromine or organochlorine compound which is added to the oil is increased. This is feasible so long as there are no deleterious effects on the operation of the engine. In practice, additions of about 5 volume percent (200 milliliters added to 4.3 liters of oil) of bromine compounds have been found to produce a usable signal without adversely affecting the operation of an engine.

For bromine tracers, there are two naturally occurring isotopes, $^{79}$Br and $^{81}$Br, with relative abundances of approximately 50.5 percent and approximately 49.5 percent, respectively. The strong infrared transitions of hydrogen bromide are in the frequency range of about 2400 to about 2700 cm$^{-1}$, with about 10 cm$^{-1}$ to about 16 cm$^{-1}$ separation between successive vibration rotation lines and with about 0.3 cm$^{-1}$ to about 0.4 cm$^{-1}$ separation between the isotopic H$^{79}$Br and H$^{81}$Br transition. In the same spectral region, there are weak carbon dioxide vibration-rotation lines. Therefore, simultaneous monitoring of HBr and CO$_2$ would enable the dynamic measurement of both fuel and oil economy at the same time.

The concentration of CO$_2$ in the exhaust gases is typically about ten percent, which is roughly 10$^6$ times higher than the concentration of HBr in the exhaust gases. Using conventional techniques, the measurement of a low concentration species may be complicated by the presence of a high concentration species. However, this difficulty is diminished using our technique due to the inverse difference in line intensities of the various gases. There are several spectral regions with adequate line spacings between the gases and with comparable line intensity values for ease of measurement. In addition, there are some spectral regions where it is feasible to measure both isotopic forms of HBr so as to provide a built-in check on the precision of this preferred laser spectrometer oil consumption measurement.

For chlorine tracers, there are two naturally occurring isotopes, $^{35}$Cl and $^{37}$Cl with naturally occurring abundances of approximately 75.5 percent and approximately 24.5 percent, respectively. The strong vibration-rotation lines are in the frequency range of approximately 2600 cm$^{-1}$ to 3100 cm$^{-1}$ where an approximately 20 cm$^{-1}$ wavenumber separation occurs between the comparable vibration-rotation lines, and where approximately 2 cm$^{-1}$ wavenumber separation occurs between the comparable vibration-rotation lines of the two isotopic molecules. It is presumed that there are spectral regions where both hydrogen chloride and carbon dioxide gas may be simultaneously measured, such as at about 2652 or about 2775 cm$^{-1}$, so as to permit concurrent dynamic measurements of oil and fuel consumption. It is also foreseeable that there are spectral regions where hydrogen chloride, hydrogen bromide and carbon dioxide may all be measured at the same time.

In accordance with U.S. Pat. No. 4,990,780 to Lee et al., tunable diode laser absorption spectroscopy has been used to measure these various components in automotive engine exhaust gas. The present invention provides improvements over the teachings of Lee et al. and utilizes either of two spectroscopic systems represented in FIGS. 1 and 4. Similar to the spectroscopic system taught by Lee et al., the spectroscopic system of FIG. 1 is characterized by the following features. First, all of the collimating and collecting optics used are preferably reflective, off-axis parabolic or focusing mirrors. This is desirable since reflective optics minimize optical interferences. Second, it is preferred to use dual beam optics for the purpose of fine tuning the laser frequency. Third, a long path multi-pass all reflection absorption cell of a White or Herriott design (as will be further discussed below) is preferably utilized to achieve the high sensitivity required for this extremely minute gas component analysis. Lastly, where windows are needed in the system, either for the tunable diode laser or the detectors or the absorption cell, tilted window holders or wedged windows are preferred so that the unwanted reflections are steered out of the optical system.

As shown in FIG. 1, the spectroscopic system includes a tunable diode laser 10 which emits an infrared laser emission 12. The laser 10 is preferably of the IV–VI compounds such as a lead chalcogenide diode laser of a buried MBE design and composed of PbEuSeTe (1.5% Eu doped), available from Laser Photonics of Andover, Mass., but may also be of the lead salt type described in U.S. Pat. Nos. 4,350,990 and 4,186,355 to Lo and 4,577,322 and 4,608,694 to Partin, or of the III–V compounds such as the GaAs types. Such lasers are coarsely tuned by varying the operating temperature and fine tuned by varying the injection current. These lasers are available for operation in the wavelength range of 2.5 to 30 microns for the lead-salt type lasers. The laser 10 may be scanned over a small band, about 0.5 to 3 cm$^{-1}$, at a ramping rate of about 500 cycles per second. The laser 10 may also be tuned to emit at a preset wavelength without scanning action to specifically target an absorption peak, for example. Alternatively, scanning or sweeping action allows the entire absorption curve related to a single line to be measured in detail. By varying the heat sink temperature and the injection current of a laser emitting at an appropriate frequency range, the laser system can be fine tuned for a variety of isotopes and molecules. Many infrared active-molecule with a suitable spectrum can be studied by this system. The system therefore would be versatile rather than dedicated to a single isotopic species. The isotopic spectral lines are well resolved, thus eliminating any background interference like that encountered in more conventional techniques.

The GaAs types of lasers mentioned above are in a class of shorter wavelength diode lasers composed of III–V compounds involving some of the following elements: Al, Ga, In, P, As and Sb. These lasers may not emit at the fundamental vibration-rotation frequencies but are utilized for combination or overtone bands along with the more sensitive detecting schemes for stable isotope analysis. These shorter wavelength lasers operate at relatively high heat sink temperatures and with shorter wavelength infrared detectors, thereby facilitating the use of inexpensive coolers such as thermoelectric coolers, or alternatively require no cooling below room temperature.

As shown in FIG. 1, the laser emission 12 is collimated with an off-axis parabolic mirror 14 and reflected by a transfer optics system composed of planar mirrors 18 through a multi-reflection sample cell 22. A suitable sample cell 22 for this invention is a "White cell" available from Infrared Analysis of Anaheim, Calif., or a "Herriott" design from Aerodyne Research, Inc., of Billerica, Mass. The laser emission 12 is preferably multi-reflected in the sample cell 22 to provide extended path lengths of as much as 104 meters, though it is foreseeable that longer path lengths could be used. Generally, longer optical path lengths enhance the exhaust signal for the HBr or HCl, but also decrease the overall intensity of the signal due to more reflection loss. Accordingly, a proper balance between the gain in signal due to absorption and the loss in signal due to reflection must be achieved. Upon leaving the sample cell 22, the laser emission 12 is reflected by a planar mirror 20 through a long focal length lens 27 to a detector, such as an InSb detector 28. The sample cell 22 is provided with exhaust gas from an internal combustion engine (not shown), as will be discussed in greater detail below. The laser 10 is tuned so that this mode spans the absorption line of the desired tracer molecule.

As shown in FIG. 1, dual beam optics are employed in which the diode laser emission is split by a beam splitter 98 through a reference cell 100 containing a standard sample of the compound to be measured in the sample cell 22. A first derivative signal from this reference cell 100 is generated by a second InSb detector 102 and is used to lock the laser frequency through a feedback control of the laser's current supply 94, which finely tunes the laser frequency. The first derivative at the line center is zero, and any drift from center will produce a positive or negative error signal which is fed back to the current supply 94.

To facilitate the alignment of the invisible infrared radiation laser emission 12, a HeNe laser 24, a cube beam splitter 16 and a pair of plane reflecting mirrors 26 may be used to properly align the laser 10, the sample cell 22 and the detector 28. During the initial setup, a grating monochromator may be used to provide wavelength identification and to filter out unwanted laser modes. Once the proper conditions for wavelength interval and single mode operation are established, the monochromator can be bypassed. The detector 28 senses the radiation which passes through the sample cell 22, and relays an appropriate signal to a signal processor, such as the personal computer (PC) shown, which processes the detector signals and provides an output on a display (not shown). The signal processor may be equipped to analyze the signal in accordance with second harmonic detection techniques.

For the preferred method, the measurement is made on a single absorption line in the spectra of the tracer isotopic specie. Such an absorption line is selected from a region free from interference or, alternatively, appropriately spaced from the other isotopic species. Though the sample essentially requires no preparation, particulate matter within the exhaust gas must be substantially eliminated in order to prevent contamination of the optical components of the sample cell, so as to ensure the long term reliability of the sampling. The sample must also be maintained at a low enough pressure within the sample cell 22 in order to eliminate pressure broadening of the spectral lines. Furthermore, water vapor within the exhaust gases must be prevented from condensing so as to prevent dissolution of the tracer compound, either HBr or HCl, in the resulting water. Such a requirement is particularly essential in view of the solubility of HBr and HCl in water.

Figure 2:
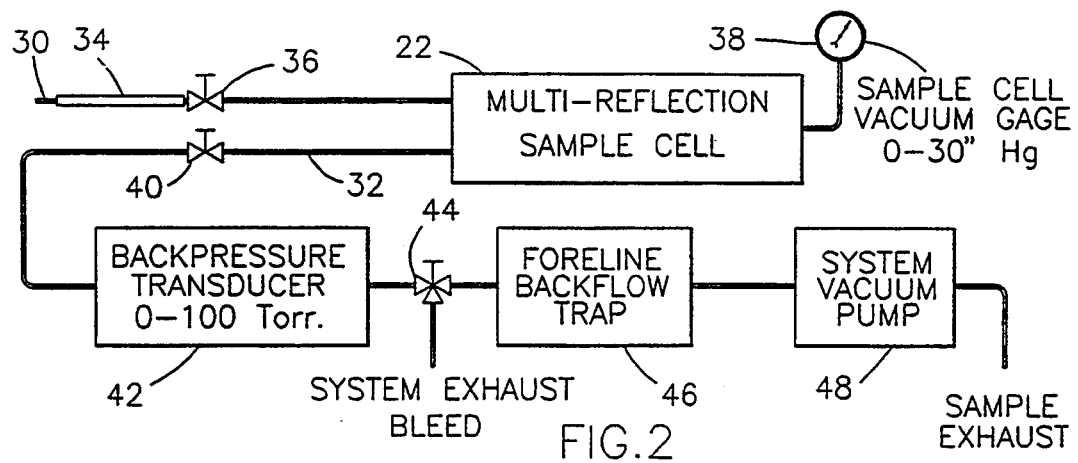
FIG. 2 is a schematic of a system plumbing diagram for use with the tunable diode laser spectrometer system of FIG. 1.

In view of the above, the present invention utilizes a sample line 34 which receives the exhaust gases directly from the engine through an exhaust inlet 30, and delivers the exhaust gas to the sample cell 22 under the required conditions. In accordance with this invention, it has been determined that the sample line 34, in cooperation with a vacuum pump 48 shown downstream of the sample cell 22 in FIG. 2, is able to reduce the pressure of the exhaust gas, such that the exhaust sample is introduced to the sample cell 22 at a pressure of no higher than about 50 torr, and more preferably at about 5 to about 20 torr. Furthermore, condensation of the water vapor within the exhaust gas is prevented by heating the sample line 34 to a temperature of about 200° C. to about 250° C., which is sufficient to prevent condensation of the water vapor even after rapid expansion as the pressure of the exhaust gas is reduced. Furthermore, it has been determined that the sample line 34 is able to substantially eliminate particulate matter within the exhaust gas, so as to prevent contamination of the optical components of the sample cell 22.

Therefore, an important aspect of the operation of the spectroscopic system is the sample line 34. In use, the sample line 34 must allow unimpeded transport of exhaust samples to the sample cell 22, while also preventing the condensation of water vapor within the system. For this purpose, the inlet to the sample line 34 is formed as a small orifice 50 upstream of a uniformly heated section 58. The heated section 58 lies immediately upstream of the sample cell 22, so as to fluidically connect the orifice 50 to the sample cell 22. As such, the exhaust gas flowing into the sample line 34 rapidly expands as it flows through the orifice 50, resulting in a pressure drop. The uniformly heated section 58 prevents water vapor condensation from occurring, while simultaneously maintaining the exhaust gas at a low and constant pressure, preferably on the order of about 5 to about 20 torr. The low exhaust gas pressure within the sample line 34 results in a dew point which is sufficiently low to allow the sample cell 22 to be operated at approximately room temperature, without an external heating source. Furthermore, it is also preferable to flow the exhaust gas through a set of staggered baffles plates (not shown) which divert the exhaust flow away from the first mirror facing the entrance to the sample cell 22, so as to prevent contamination as a result of the exhaust gas directly impinging this mirror. Finally, it has been found that the orifice 50 and the small internal diameter of the sample line 34 are able to eliminate most of the particulate matter in the exhaust gas.

Figure 3:
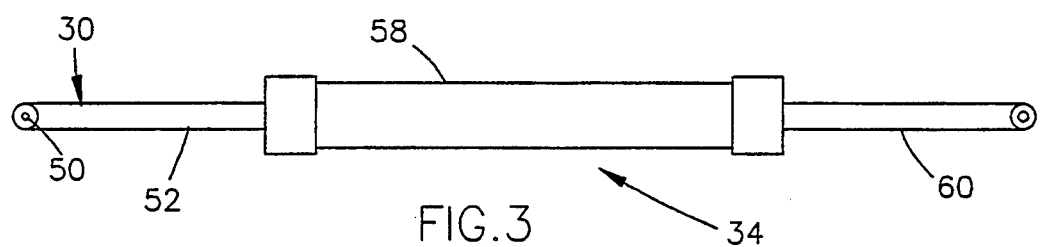
FIG. 3 is a representation of the heated sample line of FIGS. 1 and 2.

As shown in FIG. 3, the sample line 34 is generally composed of the heated section 58 and a pair of stainless steel tubes 52 and 60. Sample lines 34 having a length of about one to about four feet have been tested successfully, though it is foreseeable that an optimum length may be outside of this range in order to achieve suitable results based on the system volume, lag times, and the speed at which exhaust samples must be analyzed and recorded. Generally, the first tube 52 forms a probe which is inserted into the exhaust gas stream, and forms the exhaust inlet 30 for the sample cell 22. The end of the tubing 52 facing the exhaust inlet 30 is closed, with the orifice 50 being formed in the closed end. As noted above, the orifice 50 is sized such that the exhaust gas will rapidly expand as it travels through the orifice 50, causing a pressure drop to occur in the exhaust gas. In practice, an orifice 50 having a diameter of about 1.5 millimeters (about 1/16 inch) has been found to perform suitably when used in conjunction with roughly a 6 millimeter (about ¼ inch) diameter tube 52, though it is foreseeable that other matched orifice and tube sizes could be used. In addition, those skilled in the art will recognize that the sample line 34 could be structured and configured differently from that illustrated in FIG. 3. For example, an effective orifice for reducing the pressure of the exhaust gas sample could be formed with an internally tapered tube. Accordingly, the teachings of this invention are not to be construed as being limited to the sample line 34 shown in FIG. 3.

As indicated in FIG. 2, due to the ability of the sample line 34 to eliminate most of the particulate mauer in the exhaust gas, the system plumbing of this invention does not utilize a filtering system, in contrast to the teachings of U.S. Pat. No. 4,990,780 to Lee et al. As also indicated in FIG. 2, in a preferred embodiment a valve 36 is provided between the sample line 34 and the sample cell 22 in order to meter the appropriate amount of exhaust gas from the engine. Most preferably, the valve 36 is a ⅜ inch needle valve with a teflon seat. A vacuum gage 38 is used to monitor the system vacuum, and a ball valve 40 is preferably provided downstream of the sample cell 22 in order to facilitate system leak checks using the vacuum gage 38. A pressure transducer 42, such as an MKS Baratron 0 to 100 torr transducer available from MKS Industries, is located further downstream from the sample cell 22 for the purpose of measuring the system pressure. A ⅜ inch gate valve 44 is installed further downstream to allow relieving the system vacuum, and a foreline trap 46 is preferably located between the gate valve 44 and the system vacuum pump 48 in order to eliminate back-flow contamination from the pump 48, which would otherwise possibly result in fogging of the sample cell mirrors.

In operation, radiation at the frequency of an absorption line of the isotopic tracer specie of interest is transmitted through the sample cell 22 and its intensity, I, is measured after passing through the sample cell 22. To determine the absolute concentration value, a measure of the incident radiation intensity, $I_o$, is needed. That value is obtained by evacuating the sample cell 22 and measuring the intensity of the transmitted radiation at the same frequency after passing through the evacuated sample cell 22. An alternative method for obtaining the incident radiation intensity, $I_o$, is by turning the frequency of the radiation to a value, $f_o$, just off the absorption line, that is, near the absorption line but not subject to absorption by that line. The concentration of the tracer specie is determined from the Beer-Lambert law: $I = I_o e^{-\alpha p l}$, where "$\alpha$" is the spectral absorption coefficient of the tracer molecule, "p" is the pressure of the tracer molecule in torr, and "l" is the path length (in centimeters). This spectroscopic measurement technique is useful for a large tracer specie concentration. It is also useful for a small tracer specie concentration if cumulative concentration signals from repeated cumulative spectral scans are used.

For low tracer specie concentration, it is preferable to use a wavelength modulation and harmonic detection technique which provides a superior signal-to-noise ratio compared to a conventional straight absorption measurement. As the diode laser 10 is tuned over the spectral feature of interest, the wavelength of measurement is modulated at high frequency, such as about one to about twelve kilohertz, and with a window on the order of the spectral linewidth. The output of the detector 28 is processed by a frequency and phase selective amplification system (such as a lock-in amplifier) which is referenced to the modulation frequency. When the detection system is tuned to the second harmonic of the modulation frequency, the output is proportional to the second derivative of the spectral signal. The wavelength modulation is, in effect, averaging the spectral signal a number of times over a small window for each data point. It is important to note that the method is insensitive to any DC component of the signal such as the broad luminescence background emission that may be present in the laser 10. The spectral peak is related to the concentration of the measured specie by a working curve obtained by calibration of the spectrometer using calibration samples of known concentration, such as a permeation device. This technique is exceptionally good for measurement of very low concentrations, but a simpler and more direct technique, as described above, may be used where larger concentrations are to be measured.

To reduce signal noise during operation, various techniques may be necessary, depending on the type and source of the noise. Electrical noise arising from an AC source and picked up by the detector 28 as a radiant signal may be minimized or eliminated by proper shielding and grounding. Optical noise arising from interference fringes may be minimized or eliminated by utilizing wedged windows in the sample cell 22, and by placing a filter, such as a silicon wafer used in microelectronic fabrication, and an aperture in front of the detector 28. Finally, mechanical noise arising from the rattling of the reflective mirrors within the sample cell 22 may be minimized or eliminated by modifying the mounting fixtures in the sample cell 22.

To further enhance the operation of the spectroscopic system when using bromine as the tracer compound, a chloro-compound such as ethylene dichloride may be added to the fuel in amounts of about 4 milliliters per gallon in order to ensure transport of HBr to the sample cell 22. Upon combustion, the resulting HCl will be present in greater quantities than the HBr from the oil, and will saturate available active sites in the sample line 34 with which the HBr would otherwise react, resulting in the HBr adsorbing on the surface of the sample line 34 instead of being transported to the sample cell 22. The use of a chloro-compound in the fuel also provides a good tag for various fuel studies which may be conducted simultaneously with oil consumption measurements.

In operation, measurements of exhaust gas compositions with the spectroscopic system of this invention will be from engine or stationary vehicle tests, such as those conducted on a chassis dynamometer. With reference to FIG. 1, undiluted exhaust gas is drawn from the exhaust manifold of the test engine (not shown) through the sample line 34 which, as described above, heats the gas to a temperature of about 200° C. to about 250° C. while simultaneously reducing the pressure of the gas to about 50 torr or less. As such, an exhaust gas sample is obtained at a suitable pressure for analysis, without losing the trace compound to water condensation. The exhaust gas sample is then introduced into the sample cell 22, where it is maintained at the desired pressure by the vacuum pump 48. Monochromatic light at the desired wavelength is transmitted through the sample cell 22 by means of the preferred tunable diode laser 10, which is maintained at a set temperature by a temperature controller 92 and electrically connected to a current control module 94. The detector 28 analyzes the spectroscopic signals and furnishes the measurements to a computer 96 for further analysis. The exhaust gas sample continues to flow through the sample cell 22 via an exhaust outlet 32, from which the sample eventually flows out of the plumbing system.

The exact dimensions of the sample volume will depend on which isotopic forms of the hydrogen bromide or hydrogen chloride are being used as the tracer for detection of oil consumption. However, in either alternative, after the operating conditions are determined, the volume of the sample cell 22 is minimized to promote rapid throughput of the gas for the best time resolution of the signal. The actual time resolution is measured by determining instrument response to a bolus of test gas introduced at the exhaust inlet 30 and the system dimensions adjusted to maximize performance.

In accordance with the teachings of this invention, as well as U.S. Pat. No. 4,990,780 to Lee et al., it is anticipated that this configuration is able to simultaneously monitor fuel consumption and oil consumption during conventional multi-mode emission tests and other dynamometer tests of engines or whole vehicles. Measurements of this type taken over very short periods of time, i.e., seconds or minutes, allow comparisons to be made of the effects of component-design modifications on fuel and oil consumption over a wide range of engine operating conditions. This type of testing is not possible with drain-weigh or dipstick techniques due to the inaccuracy and long run time necessary to make such measurements. In addition, this system permits the use of a non-radioactive tracer compound in the fuel and/or oil.

Finally, in accordance with the above, the teachings of this invention are an improvement over the teachings of U.S. Pat. No. 4,990,780 to Lee et al., in that the sample line 34 provides a single structure by which the pressure of a clean exhaust gas sample can be reduced to a suitable level, and simultaneously heated sufficiently so as to prevent water vapor in the rapidly expanded exhaust gas from condensing. As a result, proper flow through the sample cell 22 and proper pressure within the sample cell 22 is achieved, while enabling the tracer compound and water vapor to coexist in the exhaust gas sample as it is analyzed within the sample cell 22. Furthermore, the configuration of the sample line 34 of this invention has been found to substantially eliminate particulate matter within the exhaust gas from contaminating the optical components of the sample cell 22, so as to ensure the accuracy of the sampling. As a result, the conventional requirement for upstream filters to remove particulate matter within the exhaust gas has been eliminated.

Figure 4:
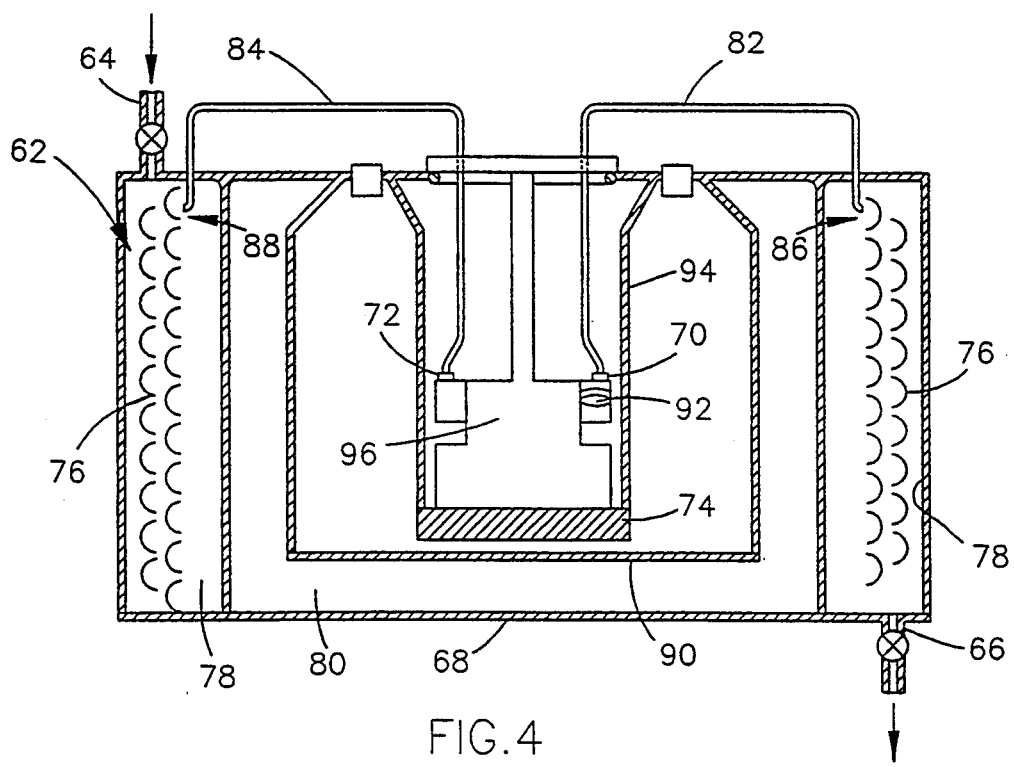
FIG. 4 shows a schematic of a tunable diode laser spectrometer system in accordance with a second embodiment of this invention.

In accordance with the second embodiment of this invention, the spectroscopic system represented in FIG. 4 generally replaces the optical system and sample cell 22 illustrated in FIG. 1 with a more rugged structure, yet retains the advantageous features of the first embodiment noted above. Similar to the spectroscopic system of FIG. 1, the spectroscopic system of FIG. 4 includes a tunable diode laser 70, a detector 72, and a sample cell 62. As before, the heated sample line 34 (not shown) of this invention is preferably located immediately upstream of the sample cell 62. The tunable diode laser 70 is preferably of the same design as that described for the diode laser 10 of FIG. 1, namely of the IV-VI compounds such as a lead chalcogenide diode laser of a buried MBE design. As before, the detector 72 is preferably an InSb detector, and senses the radiation which passes through the sample cell 62.

The spectroscopy system of this embodiment differs considerably from the embodiment of FIG. 1 in that the optical system, composed of the plane mirrors 18 and 20, and the sample cell 22, composed of a multi-pass all reflection absorption cell, are replaced by the sample cell 62, which more accurately may be described as a waveguide sample cell. Due to its construction, the sample cell 62 is suitable for use under conditions where a more rugged sample cell is desired. Yet the sample cell 62 is also able to achieve the high sensitivity required for the extremely minute gas component analysis required of this invention.

Generally, the sample cell 62 is composed of a cylindrical housing 68 with an exhaust inlet 64 and an exhaust outlet 66. Though not shown, the heated sample line 34 of this invention is connected immediately upstream of the exhaust inlet 64 in much the same manner as described for the sample cell 22 of FIG. 1. Centrally disposed within the housing 68 is an enclosure 94 which houses a mounting block 96 supporting the diode laser 70 and the detector 72. The enclosure 94 is preferably suspended within a bath of liquid nitrogen contained in an annular-shaped tank 90, which is also suspended within the housing 68. The base of the enclosure 94 forms a cold finger 74 which serves as a cold sink for the mounting block 96 and the diode laser 70. A heater 92 is provided in order to maintain the diode laser 70 at its appropriate operating temperature, which is above the temperature of the liquid nitrogen bath. Surrounding the tank 90 is a vacuum chamber 80 which insulates the tank 90 from an annular-shaped sample chamber 78 that circumscribes the vacuum chamber 80, the tank 90 and the enclosure 94.

The sample chamber 78 houses a waveguide 76, which is composed of coils of whispering gallery waveguides. Essentially, the coils form a continuous arcuate optical path through the sample chamber 78, such that a laser beam directed at an entrance 86 of the waveguide 76 will travel along a spiral-shaped path through the sample chamber 78, and exit the waveguide 76 at its opposite end 88. As shown, a laser beam generated by the diode laser 70 is directed to the entrance 86 of the waveguide 76 through an optical fiber 82, while the laser beam is directed toward the detector 72 with a second optical fiber 84 as it exits the opposite end 88 of the waveguide 76.

The operation of the spectroscopy system of FIG. 4 is essentially the same as that for the system of FIG. 1.

Undiluted exhaust gas is drawn from the exhaust manifold of the test engine through the sample line 34 which, as described above, heats the gas to a temperature of about 200° C. to about 250° C. while simultaneously reducing the pressure of the gas to about 50 torr or less. As such, an exhaust gas sample is obtained at a suitable pressure for analysis, without losing the trace compound to water condensation. The exhaust gas sample is then introduced through the exhaust inlet 64 into the sample cell 62, where it is maintained at the desired pressure using a suitable vacuum pump, such as the vacuum pump 48 represented in FIG. 2. Monochromatic light at the desired wavelength is transmitted through the sample cell 62 by means of the tunable diode laser 70, and the detector 72 subsequently analyzes the spectroscopic signals and furnishes the measurements to a computer (not shown) for further analysis. The exhaust gas flows through the sample cell 62, continuously exiting through the exhaust outlet 66, from which the sample eventually flows out through the plumbing system shown in FIG. 2.

Though structural differences exist between the spectroscopic systems of FIGS. 1 and 4, the system of FIG. 4 retains the advantageous capabilities noted with the system of FIG. 1, including the ability to monitor fuel consumption and oil consumption during dynamometer tests of engines or whole vehicles, the ability to take such measurements over very short periods of time, and the use of a nonradioactive tracer compound. In addition, the system of FIG. 4 advantageously utilizes the sample line 34, which provides a single structure by which the pressure of an exhaust gas sample can be reduced to a suitable level with a vacuum pump downstream of the sample cell 62, and simultaneously heated sufficiently so as to prevent water vapor in the rapidly expanded exhaust gas from condensing. As a result, proper flow and pressure of a clean exhaust gas sample within the sample cell 62 are achieved, while enabling the tracer compound and water vapor to coexist in the exhaust gas sample as it is analyzed.

While our invention has been described in terms of a preferred embodiment, it is apparent that other forms could be adopted by one skilled in the art, such as by the use of different laser materials, cooling techniques, or the use of fiber optics; alternative plumbing schemes; and alternative configurations for the sample line 34, as well as other modifications. Accordingly, the scope of our invention is to be limited only by the following claims.

The embodiments of the invention in which an exclusive property or privilege is claimed are defined as follows:

1. A method for evaluating fuel and engine oil consumption on a near real-time basis in an internal combustion engine, the method comprising the steps of:

treating the fuel or engine oil with a nonradioactive tracer compound either in its natural isotopic abundance or enriched, the nonradioactive tracer compound being one or more compounds selected from the group consisting of organobromine compounds and organochlorine compounds, such that the exhaust gas of the internal combustion engine contains a tracer compound comprising a tracer isotopic specie;

continuously flowing an exhaust gas sample from the internal combustion engine through a sample line in which the exhaust gas sample is rapidly expanded so as to attain a reduced pressure and in which the exhaust gas sample is heated so as to substantially prevent water vapor present in the exhaust gas from condensing while the exhaust gas is at the reduced pressure;

maintaining the exhaust gas sample at the reduced pressure within a sample cell downstream of the sample line, the sample line causing the dew point of the exhaust gas sample to be sufficiently low so as to allow the sample cell to be operated at approximately room temperature and so as to enable the tracer compound and water vapor to coexist within the sample cell, such that a distinction between an absorption line of the tracer isotopic specie and the absorption lines of related isotopic species is discernible; and transmitting monochromatic radiation through the exhaust gas sample in the sample cell at the frequency of an absorption line for the tracer isotopic specie, while concurrently detecting the intensity of a spectral line for the tracer isotopic specie so as to determine fuel and engine oil consumption in the internal combustion engine on a near real-time basis.

2. A method as recited in claim 1 wherein the tracer compound is hydrogen bromide or hydrogen chloride.

3. A method as recited in claim 1 wherein the exhaust gas sample is rapidly expanded by flowing through an orifice in the sample line.

4. A method as recited in claim 1 further comprising the step of using the sample line to substantially prevent particulate matter within the exhaust gas sample from entering the sample cell.

5. A method as recited in claim 1 wherein the step of transmitting monochromatic radiation through the exhaust gas sample in the sample cell comprises guiding the monochromatic radiation through the sample cell with a waveguide.

6. A method as recited in claim 1 wherein the tracer compound is hydrogen bromide, the method further comprising the step of adding a chloro-compound to the fuel or engine oil such that, upon combustion, hydrogen chloride will be present in the exhaust gas sample in greater quantities than hydrogen bromide, and will saturate available active sites in the sample line with which the hydrogen would otherwise react, so as to ensure transport of the hydrogen bromide to the sample cell.

7. In a method for evaluating fuel and engine oil consumption on a near real-time basis in an internal combustion engine, wherein the fuel or engine oil is treated with a nonradioactive tracer compound either in its natural isotopic abundance or enriched, the nonradioactive tracer compound being one or more compounds selected from the group consisting of organobromine compounds and organochlorine compounds, such that the exhaust gas of the internal combustion engine contains a tracer compound comprising a tracer isotopic specie; and wherein an exhaust gas sample continuously flows from the internal combustion engine through a sample cell in which the exhaust gas sample is maintained at a reduced pressure such that a distinction between an absorption line of the tracer isotopic specie and the absorption lines of related isotopic species is discernible; and wherein monochromatic radiation is transmitted through the exhaust gas sample in the sample cell at the frequency of an absorption line for the tracer isotopic specie, while concurrently detecting the intensity of a spectral line for the tracer isotopic specie, so as to determine fuel and engine oil consumption in the internal combustion engine on a near real-time basis; the improvement comprising the step of:

continuously flowing the exhaust gas sample through a sample line in which the exhaust gas sample is rapidly expanded so as to attain the reduced pressure in the sample cell, and in which the exhaust gas sample is heated so as to substantially prevent water vapor present in the exhaust gas from condensing while the exhaust gas is at the reduced pressure, the sample line causing the dew point of the exhaust gas sample to be sufficiently low so as to allow the sample cell to be operated at approximately room temperature and so as to enable the tracer compound and the water vapor to coexist within the sample cell.

8. A method as recited in claim 7 wherein the tracer compound is hydrogen bromide or hydrogen chloride.

9. A method as recited in claim 7 wherein the exhaust gas sample is rapidly expanded by flowing through an orifice in the sample line.

10. A method as recited in claim 7 further comprising the step of using the sample line to substantially prevent particulate matter within the exhaust gas sample from entering the sample cell.

11. A method as recited in claim 7 further comprising the step of guiding the monochromatic radiation through the exhaust gas sample in the sample cell with a waveguide.

12. A method as recited in claim 7 wherein the tracer compound is hydrogen bromide, the method further comprising the step of adding ethylene dichloride to the fuel or engine oil such that, upon combustion, hydrogen chloride will be present in the exhaust gas sample in greater quantities than hydrogen bromide, and will saturate available active sites in the sample line with which the hydrogen bromide would otherwise react, so as to ensure transport of the hydrogen bromide to the sample cell.

* * * * *